US00PP32508P2

(12) United States Plant Patent
Schroll

(10) Patent No.: US PP32,508 P2
(45) Date of Patent: Nov. 24, 2020

(54) ***HYDRANGEA* PLANT NAMED 'SCHROLL115-13-02'**

(50) Latin Name: *Hydrangea macrophylla*
Varietal Denomination: SCHROLL115-13-02

(71) Applicant: Soren Schroll, Odense SV (DK)

(72) Inventor: Soren Schroll, Odense SV (DK)

(73) Assignee: SCHROLL MANAGEMENT ApS, Odense SV (DK)

( * ) Notice: Subject to any disclaimer, the term of this patent is extended or adjusted under 35 U.S.C. 154(b) by 0 days.

(21) Appl. No.: 16/873,042

(22) Filed: Jan. 21, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Hydrangea* plant named 'SCHROLL115-13-02', characterized by its upright and mounded plant habit; moderately vigorous to vigorous growth habit; freely branching habit and strong dark greyed purple-colored stems; dark green-colored leaves; large mophead-type inflorescences with light red purple-colored sterile flowers with darker red purple-colored margins and venation; when "blued", that is, treated with aluminum sulfate, sterile flowers are light violet blue in color; long flowering period; and good postproduction quality and longevity.

3 Drawing Sheets

Figure 1:
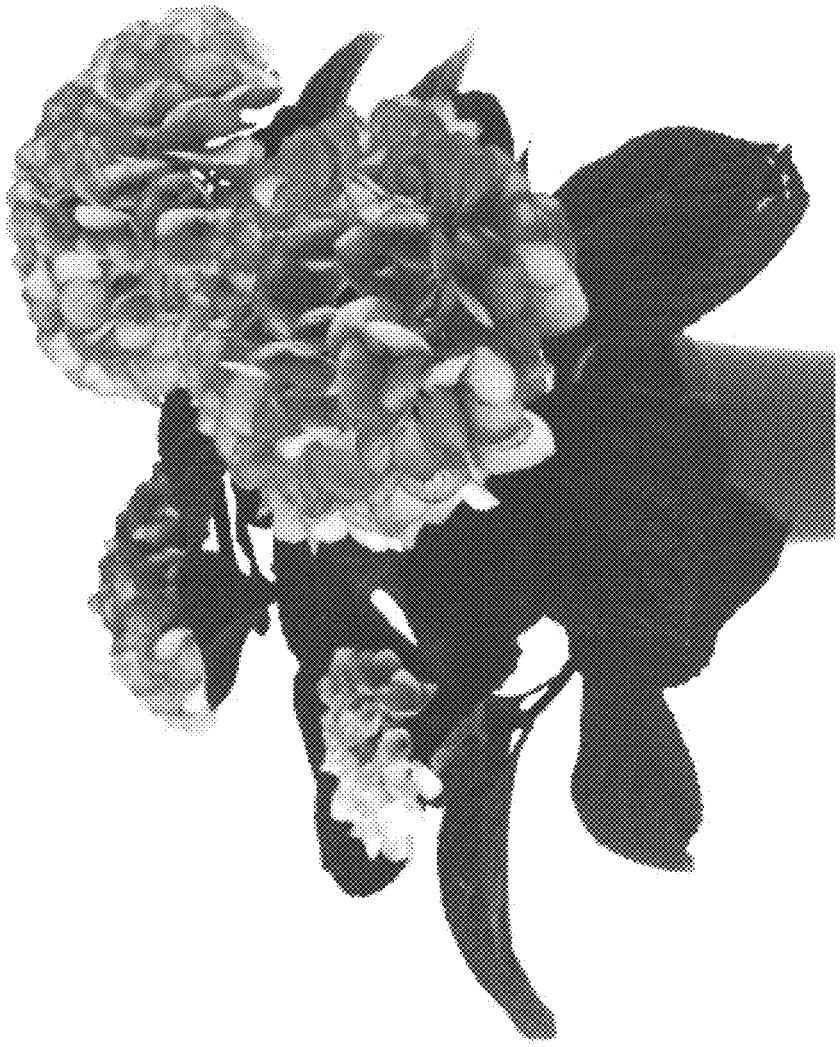

Botanical designation: *Hydrangea macrophylla.*
Cultivar denomination: 'SCHROLL115-13-02'.

BACKGROUND OF THE INVENTION

The present invention relates to a new and distinct cultivar of *Hydrangea* plant, botanically known as *Hydrangea macrophylla* and hereinafter referred to by the name 'SCHROLL115-13-02'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant is a naturally-occurring whole plant mutation of *Hydrangea macrophylla* 'SchrollA17', not patented. The new *Hydrangea* plant was discovered and selected by the Inventor in 2017 as a single flowering plant from within a population of plants of 'SchrollA17' in a controlled greenhouse environment in Aarslev, Denmark.

Asexual reproduction of the new cultivar by softwood cuttings in Aarslev, Denmark since 2017 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL115-13-02'. These characteristics in combination distinguish 'SCHROLL115-13-02' as a new and distinct *Hydrangea* plant:

1. Upright and mounded plant habit.
2. Moderately vigorous to vigorous growth habit.
3. Freely branching habit and strong and dark greyed purple-colored stems.
4. Dark green-colored leaves.
5. Large mophead-type inflorescences with light red purple-colored sterile flowers with darker red purple-colored margins and venation; when "blued", that is, treated with aluminum sulfate, sterile flowers are light violet blue in color.
6. Long flowering period.
7. Good postproduction quality and longevity.

Plants of the new *Hydrangea* differ primarily from plants of the mutation parent, 'SchrollA17', in the following characteristics:

1. Plants of the new *Hydrangea* are not as vigorous as plants of 'SchrollA17'.
2. Plants of the new *Hydrangea* have darker green-colored leaves than plants of 'SchrollA17'.
3. Inflorescences of plants of the new *Hydrangea* are more dense than inflorescences of plants of 'SchrollA17'.
4. Plants of the new *Hydrangea* and 'SchrollA17' differ in sterile flower color as sterile flowers of plants of the new *Hydrangea* are light red purple in color with darker red purple-colored margins and venation whereas sterile flowers of plants of 'SchrollA17' are soft pink in color with less distinct venation.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the *Hydrangea* are shorter than and not as vigorous as plants of 'H213901'.
2. Leaves of plants of the new *Hydrangea* are darker green in color than leaves of plants of 'H213901'.
3. Inflorescences of plants of the new *Hydrangea* are larger than inflorescences of plants of 'H213901'.
4. Sepals of sterile flowers of the new *Hydrangea* are not as undulate as sepals of sterile flowers of 'H213901'.
5. Plants of the new *Hydrangea* and 'H213901' differ in sterile flower color as sterile flowers of plants of the new *Hydrangea* are light red purple in color with darker red purple-colored margins and venation whereas sterile flower of plants of 'H213901' are dark red purple in color.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* are less vigorous than plants of 'H213906'.
2. Plants of the new *Hydrangea* force faster than plants of 'H213906'.
3. Plants of the new *Hydrangea* and 'H213906' differ in sterile flower color as sterile flowers of plants of the new *Hydrangea* are light red purple in color with darker red purple-colored margins and venation whereas sterile flowers of plants of 'H213906' are dark pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 3) comprises a side perspective view of a typical flowering plant of 'SCHROLL115-13-02' grown in a container that has not been "blued".

Figure 2:
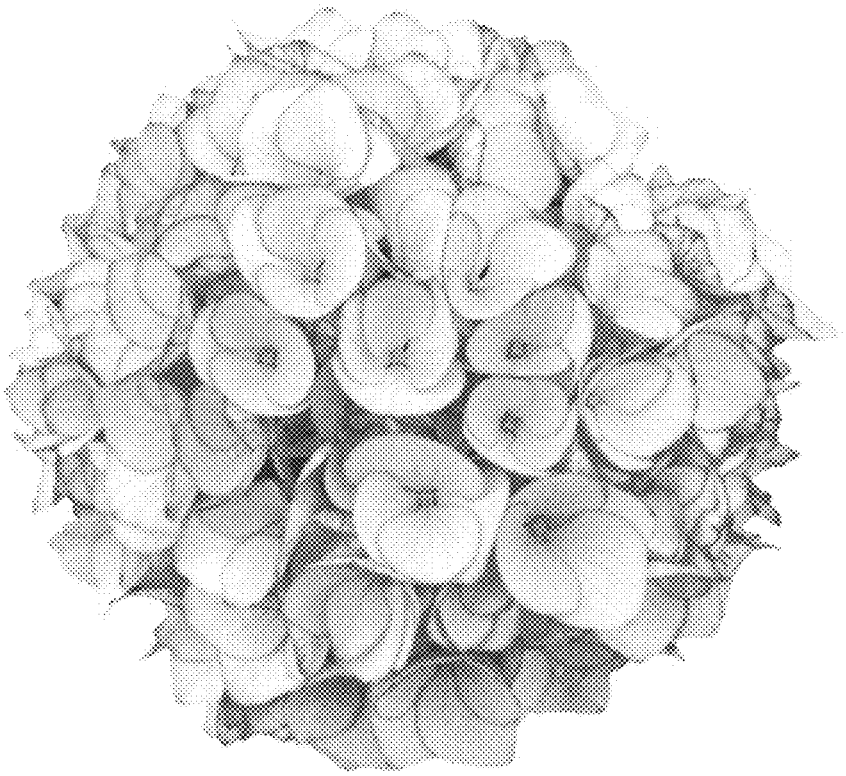

The photograph on the second sheet (FIG. 2 of 3) is a close-up view of a typical inflorescence of 'SCHROLL115-13-02' that has not been "blued".

Figure 3:
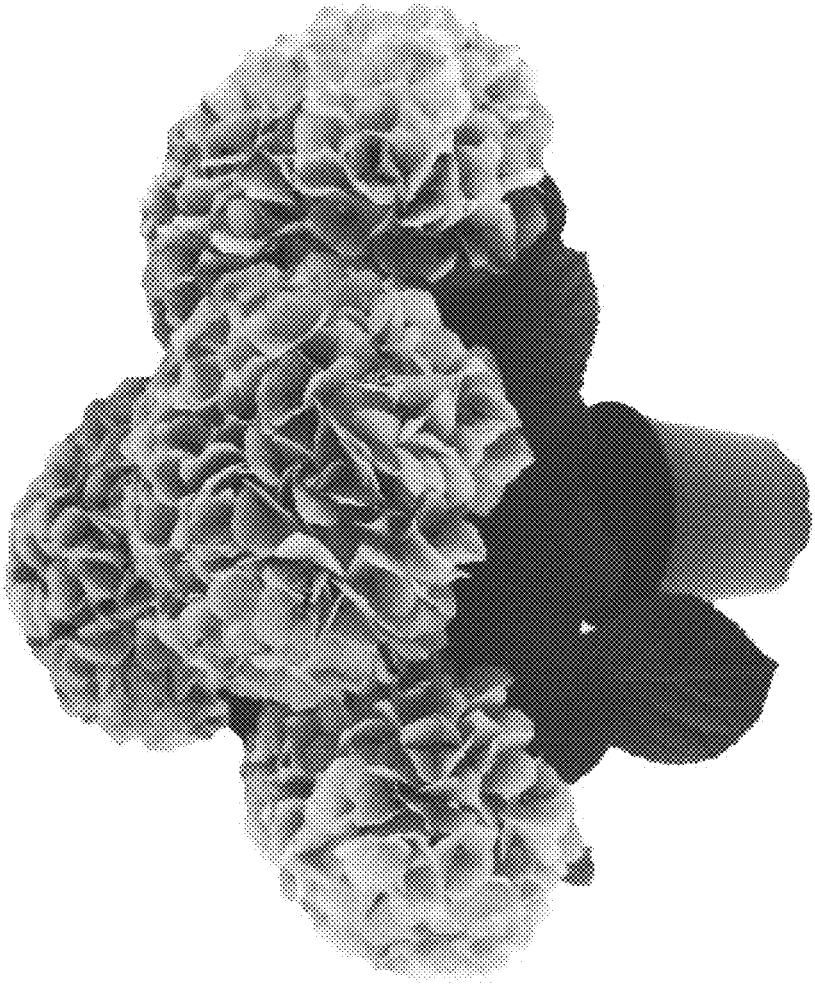

The photograph on the third sheet (FIG. 3 of 3) comprises a side perspective view of a typical flowering plant of 'SCHROLL115-13-02' grown in a container that has been "blued".

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched two times and were one year old when the photographs and description were taken. During the production of the plants, day temperatures ranged from 15° C. to 25° C. and night temperatures ranged from 10° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLL115-13-02'.

Parentage: Naturally-occurring whole plant mutation of *Hydrangea macrophylla* 'SchrollA17', not patented.

Propagation:

*Type cutting*.—By softwood cuttings.

*Time to initiate roots, summer*.—About two weeks at temperatures about 20° C.

*Time to initiate roots, winter*.—About 17 to 18 days at temperatures about 18° C. to 20° C.

*Time to produce a rooted young plant, summer*.—About four weeks at temperatures about 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Moderately freely branching; medium density.

Plant description:

*Plant and growth habit*.—Perennial subshrub; upright and mounded plant habit; broadly inverted triangle; freely branching habit with about four to six lateral branches developing per plant; strong lateral branches; moderately vigorous growth habit.

*Plant height*.—About 20 cm to 25 cm.

*Plant diameter or area of spread*.—About 35 cm to 45 cm.

*Lateral branches*.—Length: About 12 cm to 14 cm. Diameter: About 5 mm to 7 mm. Internode length: About 3 cm to 5 cm. Strength: Strong, sturdy. Texture: Smooth, glabrous. Color, developing: Close to 61A. Color, developed: Close to N186B. Color, lenticels: Close to N199B.

Leaf description:

*Arrangement*.—Opposite, decussate; simple.

*Length*.—About 10 cm to 12 cm.

*Width*.—About 7 cm to 9 cm.

*Shape*.—Ovate.

*Apex*.—Cuspidate.

*Base*.—Attenuate to decurrent.

*Margin*.—Dentate to serrate.

*Texture, upper surface*.—Smooth to rugose, glabrous.

*Texture, lower surface*.—Rugose, glabrous.

*Venation pattern*.—Pinnate, reticulate.

*Color*.—Developing leaves, upper surface: Close to 139A. Developing leaves, lower surface: Close to between 137B and 139A. Fully expanded leaves, upper surface: Close to 139A; venation, close to 139D. Fully expanded leaves, lower surface: Close to between 137B and 138A; venation, close to 139D, proximally tinged with pink.

*Petioles*.—Length: About 1 cm to 2 cm. Diameter: About 3 mm to 5 mm. Strength: Strong. Texture, upper and lower surfaces: Smooth, glabrous. Color, upper surface: Close to 144A. Color, lower surface: Close to 144B.

Inflorescence & flower description:

*Flower type and habit*.—Showy single sterile and inconspicuous single fertile flowers arranged on terminal mophead-type panicles; panicles hemispherical to slightly flattened globular in overall shape; fertile flowers face upright and sterile flowers face upright to outwardly depending on their position on the inflorescence; early flowering habit, plants begin flowering about eight to nine weeks after forcing period.

*Natural flowering season*.—Long flowering period, continuous flowering from the late summer (August) until frost in Northern Europe.

*Flower longevity, fertile flowers*.—Flowers last about one month on the plant; fertile flowers not persistent.

*Flower longevity, sterile flowers*.—Flowers last about 120 to 150 days on the plant; sterile flowers persistent.

*Quantity of flowers*.—Freely flowering habit with about 20 fertile flowers and about 60 sterile flowers per panicle.

*Fragrance*.—None detected.

*Panicle height*.—About 8 cm to 10 cm.

*Panicle diameter*.—About 18 cm to 20 cm.

*Flower diameter, fertile flowers*.—About 7 mm to 8 mm.

*Flower depth (height), fertile flowers*.—About 3 mm to 4 mm.

*Flower diameter, sterile flowers*.—About 4 cm to 6 cm.

*Flower depth (height), sterile flowers*.—About 2 cm.

*Flower shape, fertile flowers*.—Spherical.

*Flower shape, sterile flowers*.—Rounded.

*Flower buds, fertile flowers*.—Length: About 3 mm. Diameter: About 3 mm. Shape: Spherical. Color: Close to 144D.

*Flower buds, sterile flowers*.—Length: About 3 mm. Diameter: About 3 mm. Shape: Spherical. Color: Close to 144C to 144D.

*Petals, fertile flowers*.—Quantity and arrangement: Five in a single whorl. Length: About 4 mm to 5 mm. Width: About 1 mm to 2 mm. Shape: Deltoid, valvate. Apex: Acute. Base: Cuneate. Margin: Entire. Texture, upper and lower surfaces: Smooth, glabrous. Color: When opening, upper and lower surfaces: Close to 149D with margins, close to 62A; when "blued", close to 149D with margins, close to 95B. Fully opened, upper surface: Close to 62A with margins, close to 70B, color does not change with development; when "blued", close to 97A with margins, close to 96C, with development becoming closer to 138A to 138C with margins, close to 59B. Fully opened, lower surface: Close to 62A with margins, close to 70B, color does not change with development; when "blued", close to 97A with margins, close to 96C, with development becoming closer to 141C with venation, close to 59A.

*Petals, sterile flowers*.—Quantity and arrangement: If present, four or five in a single whorl. Length: About 3 mm to 4 mm. Width: About 2 mm. Shape: Ovate. Apex: Acute. Base: Rounded to truncate. Margin: Entire to denticulate. Texture, upper and lower surfaces: Smooth, glabrous. Color: When opening, upper and lower surfaces: Close to 90D; when "blued", close to 90B. Fully opened, upper and lower surfaces: Close to 62C; when "blued", close to 91C; color does not change with development.

*Sepals, fertile flowers*.—Quantity and arrangement: About five in a single whorl; sepals are malformed and vary in shape and size. Texture, upper surface: Smooth, glabrous. Texture, lower surface: Pilose. Color: When opening and fully opened, upper surface: A mixture of close to 145C and 145D with margins and venation, close to N66B; when "blued", a mixture of 145A to 145D with margins and venation, close to 61A and 61B; color does not change with development. When opening and fully opened, lower surface: A mixture of close to 145C and 145D with margins and venation, close to N66B; when "blued", a mixture of 145A to 145D with margins and venation, close to 61A and 61B; color does not change with development.

*Sepals, sterile flowers*.—Quantity and arrangement: Four in a single whorl. Length: About 3 cm. Width: About 3.5 cm. Shape: Deltoid to ovate. Apex: Obtuse. Base: Broadly cuneate. Margin: Entire; apex, occasionally emarginate. Texture, upper and lower surfaces: Smooth, glabrous. Color, plants not "blued": When opening, upper and lower surfaces: Close to 62D; margins and venation, close to N74A. Fully opened, upper surface: Close to 62B to 62D; margins and venation, close to N74A; greenish tinge appears with development. Fully opened, lower surface: Close to 65D; margins and venation, close to N74A; greenish tinge appears with development. Color, plants "blued": When opening, upper and lower surfaces: Close to 92C to 92D. Fully opened, upper surface: Close to 85D; greenish tinge appears with development. Fully opened, lower surface: Close to 98D; greenish tinge appears with development.

*Pedicels, fertile flowers*.—Length: About 1 cm to 1.5 cm. Diameter: About 1 mm. Strength: Strong. Aspect: Mostly upright to outwardly. Texture: Pilose. Color: Close to N79A.

*Pedicels, sterile flowers*.—Length: About 3.5 cm. Diameter: About 1.5 mm. Strength: Strong. Aspect: About 45° from vertical. Texture: Pubescent. Color, plants not "blued": Close to 64A. Color, plants "blued": Close to 71A.

*Reproductive organs, fertile flowers*.—Stamens: Quantity per flower: About five. Filament length: About 1 mm to 2 mm. Filament color: Close to 155D. Anther length: About 1 mm. Anther shape: Ovate. Anther color: Close to 155D. Pollen amount: Scarce. Pollen color: Close to 155D. Pistils: Pistil quantity per flower: About three. Pistil length: Less than 1 mm. Stigma shape: Ovate. Stigma color: Close to 155D. Style length: Less than 1 mm. Style color: Close to 155D.

*Reproductive organs, sterile flowers*.—Stamens: Quantity per flower: About eight to ten. Filament length: About 2 mm to 3 mm. Filament color: Close to 155D. Anther length: About 1 mm. Anther shape: Ovate. Anther color: Close to 155D. Pollen amount: Scarce. Pollen color: Close to 4C. Pistils: To date, pistil development has not been observed on plants of the new *Hydrangea*.

*Seeds* (*on fertile flowers only*).—Quantity: About 30 to 50. Length: About 0.5 mm. Diameter: About 0.1 mm. Color: Brownish.

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to 35° C.

It is claimed:

1. A new and distinct *Hydrangea* plant named 'SCHROLL115-13-02' as illustrated and described.

* * * * *